United States Patent [19]

Dunphy et al.

[11] Patent Number: 5,108,737

[45] Date of Patent: Apr. 28, 1992

[54] COLORED COSMETIC STICKS

[75] Inventors: Patrick J. Dunphy, Wellingborough, United Kingdom; Alan J. Meyers, Trumbull, Conn.; Richard T. Rigg, Springfield Garden, N.Y.

[73] Assignee: Elizabeth Arden Co., Division of Conopco, Inc., New York, N.Y.

[21] Appl. No.: 723,355

[22] Filed: Jun. 28, 1991

[51] Int. Cl.⁵ ............. A61K 7/025; A61K 7/00
[52] U.S. Cl. ..................... 424/64; 106/404; 424/63; 424/401
[58] Field of Search ............ 424/64, 65, 70; 106/404

[56] References Cited

U.S. PATENT DOCUMENTS 2,566,722  9/1951  Friedberg .................... 424/64
3,911,105  10/1975  Papantoniou ................ 424/64
4,795,631  1/1989  Sheehan ...................... 424/64
4,822,602  4/1989  Sabatelli ..................... 424/65

FOREIGN PATENT DOCUMENTS 61-83110  4/1986  Japan.

OTHER PUBLICATIONS

JP-A-61/83110 (Konuki) 4/1986.

Primary Examiner—Thurman K. Page
Assistant Examiner—Sally Gardner
Attorney, Agent, or Firm—Milton L. Honig

[57] ABSTRACT

A colored cosmetic stick, especially a lipstick, is provided containing water, a solidifying agent such as a wax, and a colorant which is an aluminum salt, especially an aluminum lake.

6 Claims, No Drawings

COLORED COSMETIC STICKS

BACKGROUND OF THE INVENTION

1. Field of the Invention

The invention relates to a colored cosmetic stick which contains an aqueous emulsion adapted to be applied to the human skin, especially to lips.

2. The Related Art

Traditional lipsticks are formulated with hydrophobic ingredients such as oils and waxes. Water is ordinarily not present in such formulations.

There has been reported in JP-A-61/83110 (Konuki), published Apr. 26, 1986, a lipstick containing small amounts of water. Water-soluble dyes were recommended as components of the lipstick. The ready dissolution of these dyes was stated as rendering it possible to manufacture lipsticks with a fresh appearance and in a variety of colors. These dissolved dyes were also noted to have good adhesion to the lips. Specifically mentioned was red iron oxide as an inorganic pigment and Permanent Orange or Red 401 as organic pigments.

Unfortunately, there are problems with the water-soluble dyes. One of these problems concerns staining of lips in a manner which is not always quickly reversible. There are also issues of health where organic dyes are concerned.

Some types of colorants have also been found to adversely interact with other traditional components of a lipstick which in a non-aqueous formulation would ordinarily not cause any problem. Compatibility factors must, therefore, also be considered.

Accordingly it is an object of the present invention to provide a colored cosmetic stick, especially a lipstick, formulated with a water emulsion containing a colorant system that avoids staining and reduces any health risks.

A further object of the present invention is to provide a colored cosmetic stick, especially a lipstick, formulated with a water emulsion containing colorants that do not adversely interact with other components of the formulation.

It is still a further object of the present invention to provide a colored cosmetic stick, especially a lipstick, formulated with an aqueous emulsion and with both yellow and red colorants that will produce good color impact while maintaining structural and aesthetic integrity of the formulated sticks.

These and other objects, features and advantages of the present invention will become more readily apparent through consideration of the following summary, detailed description and examples which follow.

SUMMARY OF THE INVENTION

A colored cosmetic stick, especially a lipstick, is provided comprising:
(i) from about 0.5 to about 25% of water;
(ii) from about 1 to about 99% of a solidifying agent; and
(iii) from about 0.001 to about 20% of a colorant which is an aluminum salt.

Especially useful are aluminum salts in the form of aluminum lakes of organic dyes. Preferred are yellow and red aluminum lakes. It is also desirable to avoid the presence of fatty acids in amounts higher than about 0.5%.

DETAILED DESCRIPTION

Now it has been discovered that aluminum salts may successfully be utilized as colorants for cosmetic sticks, especially lipsticks, which are formulated to contain water. Sticks of the present invention will contain the following general types of ingredients.

(A) Water

The compositions will contain anywhere from about 0.5 to about 25% of water. Preferably water will constitute from about 1 to about 15%, optimally from about 3 to about 8% by weight of the composition. Water will serve as an aqueous phase carrier for the emulsion compositions and may provide a solvent for any water-soluble ingredients present in the formula.

(B) Solidifying Agent

Any hydrophobic organic solid of melting point in excess of about 20° C. and which assists in forming a solid structure for the cosmetic stick is defined for purposes of this invention as a solidifying agent. Of particular utility are waxes. The waxes are low-melting organic compounds or mixtures of high molecular weight substances, are solid at room temperature and are generally similar in composition to fats and oils, except that they contain no glycerides. Some are hydrocarbons; others are esters of fatty acids and alcohols. Waxes are thermoplastic, but since they are not high polymers, they are not considered in the family of plastics. Natural, mineral and synthetic waxes may all be employed. Among the natural waxes are those of animal origin (beeswax, spermaceti, lanolin, shellac wax), vegetable (carnauba, candelilla, bayberry, sugarcane wax) and mineral (ozokerite, ceresin, montan, paraffin, microcrystalline, petroleum and petrolatum wax). Synthetic waxes include polyol ether-esters such as "carbowax" and hydrocarbon-type waxes.

Most preferred are candelilla, ozokerite, carnauba, beeswax, lanolin and spermaceti waxes.

Care should be taken to remove any $C_{10}$–$C_{26}$ fatty acids that may be components of wax mixtures. Fatty acids have been found to react with aluminum lakes thereby forming aluminum soaps; these soaps act as crystal poisons which cause the stick to lose structure. Thus, compositions of the present invention will be formulated with less than an effective amount of a $C_{10}$–$C_{26}$ fatty acid that would otherwise form a soap with aluminum lakes. Preferably the amount of fatty acid should be no higher than about 0.5%, more preferably no higher than about 0.1%, optimally less than about 0.05% by weight.

Absence of free fatty acids may be insured by selection of raw materials that possess little if any of such material. Alternatively, raw materials such as certain waxes which inherently contain fatty acids within the natural wax may be treated through esterification for reactive removal or through solvent extraction for physical removal of the free fatty acids. Reactive removal may include ethylene oxide treatment or long-chain fatty alcohol treatment which give rise to polyethylene glycol fatty acid esters and fatty long-chain esters, respectively.

By contrast to aluminum lakes, barium and calcium lakes have no adverse interaction with free fatty acids.

Amounts of the solidifying agent may range anywhere from about 1 to about 99% by weight, preferably from about 10 to about 50%, optimally between about 15 and about 25% by weight.

(C) Colorant

Compositions of the present invention will contain from about 0.001 to about 20% by weight of a colorant which is an aluminum salt. Amounts of colorant will preferably range from about 0.1 to about 10%, optimally from about 0.5 to about 8% by weight.

Advantageously, the aluminum salt is an aluminum lake. Lakes are either a pigment that is extended or reduced with a solid diluent or an organic pigment that is prepared by the precipitation of a water-soluble dye on an adsorptive surface, which usually is alumina hydrate. There is uncertainty in some instances as to whether the soluble dye precipitates on the surface of the alumina hydrate to yield a dyed inorganic pigment or whether it merely precipitates in the presence of the substate. A lake also forms from precipitation of an insoluble salt from an acid or basic dye.

Particularly preferred aluminum lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake.

Beyond the basic components of the present invention, there optionally may be other ingredients which serve to enhance product function and aesthetics. These optional ingredients are as follows:

(1) Emulsifier System

Emulsifiers may be incorporated in the cosmetic formulations of the present invention. Overall concentration of emulsfier may range anywhere from about 0.1 to about 30% by weight of the formulation, preferably from about 0.5 to about 20%, optimally between about 2 and 10% by weight.

Phospholipids is an important category of emulsifiers that may contribute to the stability and pleasing appearance of the composition.

Examples of phospholipids are those within the categories of phosphoglycerides, lysophosphoglycerides, sphingomyelins and mixtures thereof. Especially useful as a phospholipid is lecithin.

Fatty acid derivative-type emulsifiers may also be employed, especially in combination with a phospholipid. These emulsifiers may include monoacyl glycerol, diacyl glycerol and polyglycerol esters and combinations thereof. Especially preferred are glycerol monoalkanoates, an example of which are the monoglycerides of sunflower seed oil and of palm oil.

(2) Emollient Oils

Emollient oils which are defined as oily organic substances liquid at room temperature (i.e. 20° C.) can be employed singly or as mixtures of two or more oils. They normally will be present at levels from about 2 to about 97%, preferably from about 30 to 70% by weight of the composition.

These oils are useful not only for emollient purposes but may also impart viscosity, tackiness and drag properties. Examples of suitable oils include caprylic triglycerides; capric triglycerides; isostearic triglycerides; adipic triglycerides; propylene glycol myristyl acetate; lanolin oil; polybutene; isopropyl palmitate; isopropyl myristate; diethyl sebacate; diisopropyl adipate; hexadecyl stearate; cetyl oleate; oleyl alcohol; hexadecyl alcohol; wheatgerm oil; hydrogenated vegetable oils; petrolatum; modified lanolins; branched-chain hydrocarbons, alcohols and esters; castor oil; corn oil; cottonseed oil; olive oil; palm kernel oil; rapeseed oil; safflower seed oil; jojoba oil; evening primrose oil; avocado oil; mineral oil; and volatile and non-volatile silicone oils.

(3) Skin Care Active Ingredients

Skin active ingredients in the form of both water-soluble and insoluble substances may be included within the formulations of this invention. These ingredients may range anywhere from about 0.0001 to about 10% by weight. Examples include zinc oxide; $\beta$-glycyrrhetic acid; chamomile oil; ginko biloba extract; pyroglutamic acid, salts or esters; sodium hyaluronate; 2-hydroxyoctanoic acid; sulphur; salicylic acid; carboxymethyl cysteine and mixtures thereof.

The following examples will more fully illustrate certain aspects of the present invention. All parts, percentages and proportions referred to herein and in the appended claims are by weight unless otherwise indicated.

EXAMPLE 1

A cosmetic lipstick in accordance with the invention was formulated containing the following ingredients:

| Ingredient | % Weight |
| --- | --- |
| Castor oil | 19.5 |
| Isopropyl palmitate | 11.6 |
| Caprylic/capric/isostearic/adipic triglyceride | 7.0 |
| Lanolin | 7.0 |
| Red 21 Aluminum Lake | 7.0 |
| Candelilla wax | 6.6 |
| Propylene glycol myristyl ether acetate | 6.0 |
| Caprylic/capric triglyceride | 5.8 |
| Glycerol | 5.0 |
| Water | 5.0 |
| Titanium dioxide | 4.7 |
| Beeswax | 4.1 |
| Monoglyceride | 3.5 |
| Lanolin oil | 2.5 |
| Ozokerite wax | 2.5 |
| Phospholipid (soybean lecithin) | 1.0 |
| Polybutene | 0.8 |
| Carnauba wax | 0.4 |

EXAMPLE 2

A cosmetic lipstick in accordance with the invention was formulated containing the following ingredients:

| Ingredient | % Weight |
| --- | --- |
| Castor oil | 19.5 |
| Isopropyl palmitate | 11.6 |
| Caprylic/capric/isostearic/adipic triglyceride | 7.0 |
| Lanolin | 7.0 |
| Red 27 Aluminum Lake | 7.0 |
| Candelilla wax | 6.6 |
| Propylene glycol myristyl ether acetate | 6.0 |
| Caprylic/capric triglyceride | 5.8 |
| Glycerol | 5.0 |
| Water | 5.0 |
| Titanium dioxide | 4.7 |
| Beeswax | 4.1 |
| Monoglyceride | 3.5 |
| Lanolin oil | 2.5 |
| Ozokerite wax | 2.5 |
| Phospholipid (soybean lecithin) | 1.0 |
| Polybutene | 0.8 |

EXAMPLE 3

A cosmetic lipstick in accordance with the invention was formulated containing the following ingredients:

| Ingredient | % Weight |
| --- | --- |
| Castor oil | 19.5 |
| Isopropyl palmitate | 11.6 |
| Caprylic/capric/isostearic/adipic triglyceride | 7.0 |
| Lanolin | 7.0 |
| Yellow 5 Aluminum Lake | 7.0 |
| Candelilla wax | 6.6 |
| Propylene glycol myristyl ether acetate | 6.0 |
| Caprylic/capric triglyceride | 5.8 |
| Glycerol | 5.0 |
| Water | 5.0 |
| Titanium dioxide | 4.7 |
| Beeswax | 4.1 |
| Monoglyceride | 3.5 |
| Lanolin oil | 2.5 |
| Ozokerite wax | 2.5 |
| Phospholipid (soybean lecithin) | 1.0 |
| Polybutene | 0.8 |
| Carnauba wax | 0.4 |

EXAMPLE 4

A cosmetic lipstick in accordance with the invention was formulated containing the following ingredients:

| Ingredient | % Weight |
| --- | --- |
| Castor oil | 19.5 |
| Isopropyl palmitate | 11.6 |
| Caprylic/capric/isostearic/adipic triglyceride | 7.0 |
| Lanolin | 7.0 |
| Yellow 6 Aluminum Lake | 7.0 |
| Candelilla wax | 6.6 |
| Propylene glycol myristyl ether acetate | 6.0 |
| Caprylic/capric triglyceride | 5.8 |
| Glycerol | 5.0 |
| Water | 5.0 |
| Titanium dioxide | 4.7 |
| Beeswax | 4.1 |
| Monoglyceride | 3.5 |
| Lanolin oil | 2.5 |
| Ozokerite wax | 2.5 |
| Phospholipid (soybean lecithin) | 1.0 |
| Polybutene | 0.8 |
| Carnauba wax | 0.4 |

The foregoing description and examples illustrate selected embodiments of the present invention. In light thereof, various modifications will be suggested to one skilled in the art, all of which are within the spirit and purview of this invention.

What is claimed is:

1. A colored cosmetic lipstick comprising:
   (i) from about 0.5 to about 25% of water;
   (ii) from about 1 to about 99% of a solidifying agent which is a wax;
   (iii) from about 0.001 to about 20% of a colorant which is an aluminum salt; and
   wherein said stick is formulated with no higher than about 0.5% by weight of a $C_{10}-C_{26}$ fatty acid sufficient to form an aluminum soap with said aluminum salt that would cause said lipstick to lose structure.

2. The cosmetic lipstick according to claim 1 wherein said aluminum salt is an aluminum lake.

3. The cosmetic lipstick according to claim 1 wherein said aluminum salt is selected from the group consisting of Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake, Blue 1 Aluminum Lake and combinations thereof.

4. The cosmetic lipstick according to claim 1 wherein said lipstick is formulated with less than about 0.05% by weight of a $C_{10}-C_{26}$ fatty acid.

5. The cosmetic lipstick according to claim 1 wherein said wax is selected from the group consisting of candelilla, oxokerite, carnauba, beeswax, lanolin and wax mixtures thereof.

6. The cosmetic lipstick according to claim 1 wherein said wax is present in an amount from about 10 to about 50% by weight.

* * * * *